United States Patent
Foell et al.

(10) Patent No.: US 9,177,752 B2
(45) Date of Patent: Nov. 3, 2015

(54) DEVICE FOR STERILIZING CONTAINERS BY WAY OF CHARGE CARRIERS

(75) Inventors: Eberhard Foell, Nehren (DE); Jochen Krueger, Thalmassing (DE)

(73) Assignee: KRONES AG, Neutraubling (DE)

( * ) Notice: Subject to any disclaimer, the term of this patent is extended or adjusted under 35 U.S.C. 154(b) by 665 days.

(21) Appl. No.: 12/995,086

(22) PCT Filed: May 5, 2009

(86) PCT No.: PCT/EP2009/055369
§ 371 (c)(1),
(2), (4) Date: Nov. 29, 2010

(87) PCT Pub. No.: WO2009/144114
PCT Pub. Date: Dec. 3, 2009

(65) Prior Publication Data
US 2011/0076187 A1    Mar. 31, 2011

(30) Foreign Application Priority Data
May 30, 2008 (DE) .......................... 10 2008 025 868

(51) Int. Cl.
| B01J 19/12 | (2006.01) |
| A61L 2/00 | (2006.01) |
| H01J 33/00 | (2006.01) |
| H01J 33/04 | (2006.01) |
(Continued)

(52) U.S. Cl.
CPC ................ *H01J 33/00* (2013.01); *A61L 2/087* (2013.01); *H01J 33/04* (2013.01); *A61L 2202/23* (2013.01); *B65B 55/08* (2013.01)

(58) Field of Classification Search
CPC ........... A61L 2/087; H01J 33/00; H01J 33/04
USPC .............................. 422/22, 186.05; 250/493.1
See application file for complete search history.

(56) References Cited

U.S. PATENT DOCUMENTS

| 3,133,227 A | 5/1964 | Brown et al. |
| 4,952,814 A * | 8/1990 | Huntzinger ................ 250/505.1 |
| 5,378,957 A * | 1/1995 | Kelly ....................... 313/231.01 |
(Continued)

FOREIGN PATENT DOCUMENTS

| DE | 195 18 623 A1 | 11/1996 |
| DE | 19518623 | 11/1996 |
(Continued)

OTHER PUBLICATIONS

English translation of Office Action dated Aug. 29, 2013 in corresponding Japanese Patent Application No. 2011-510927.
(Continued)

*Primary Examiner* — Kevin Joyner
(74) *Attorney, Agent, or Firm* — Onello & Mello, LLP

(57) ABSTRACT

A device for sterilizing containers may include a treatment head having an outlet window for the passing of charge carriers therethrough, a charge carrier generation source for generating charge carriers, an acceleration device disposed above the outlet window, and a cooling device for cooling the outlet window. The acceleration device accelerates the charge carriers in the direction of the outlet window. The cooling device includes a feed opening for a gaseous medium. The feed opening is disposed beneath the outlet window and directs the gaseous medium at least partially from below to the outlet window.

15 Claims, 1 Drawing Sheet

(51) Int. Cl.
*A61L 2/08* (2006.01)
*B65B 55/08* (2006.01)

(56) References Cited

U.S. PATENT DOCUMENTS

| | | | |
|---|---|---|---|
| 5,416,440 A | 5/1995 | Lyons et al. | |
| 6,221,216 B1 | 4/2001 | Nablo et al. | |
| 6,724,003 B1 * | 4/2004 | Doi et al. | 250/492.3 |
| 7,800,012 B2 | 9/2010 | Roche et al. | |
| 2001/0011710 A1 * | 8/2001 | Naito | 250/492.3 |
| 2007/0145304 A1 | 6/2007 | Roche et al. | |

FOREIGN PATENT DOCUMENTS

| | | |
|---|---|---|
| DE | 198 82 252 T1 | 5/2000 |
| DE | 101 34 037 A1 | 1/2003 |
| EP | 1 100 109 A1 | 5/2001 |
| EP | 1100109 | 5/2001 |
| EP | 1 120 121 A2 | 8/2001 |
| GB | 277 347 | 12/1928 |
| GB | 277347 | 12/1928 |
| GB | 1 255 472 | 12/1971 |
| GB | 1255472 | 12/1971 |
| JP | Shou49-8692 | 2/1974 |
| JP | Shou49-109823 | 9/1974 |
| JP | Shou49-117193 | 10/1974 |
| JP | 2002-006095 | 1/2002 |
| JP | 2003-337199 | 11/2003 |
| JP | 2007-511039 | 4/2007 |
| JP | 2007-297067 | 11/2007 |
| WO | 97/07024 A1 | 2/1997 |
| WO | 2007/095205 A2 | 8/2007 |
| WO | 2007/145561 A1 | 12/2007 |

OTHER PUBLICATIONS

International Search Report dated Aug. 5, 2009 issued in corresponding International Application No. PCT/EP2009/055369.

* cited by examiner

DEVICE FOR STERILIZING CONTAINERS BY WAY OF CHARGE CARRIERS

CROSS-REFERENCE TO RELATED APPLICATION

This application is filed under 35 U.S.C. 371 as a U.S. national phase application of PCT/EP2009/055369, having an international filing date of May 5, 2009, which claims the benefit of German Patent Application No. 10 2008 025 868.7, having a filing date of May 30, 2008, both of which are hereby incorporated by reference.

TECHNICAL FIELD

The present invention relates to an apparatus for the sterilization of containers, more specifically for the sterilization of containers before they are filled. In particular, the inner wall of containers to be filled or of bottles should be sterilized by the apparatus according to the invention. Various apparatus and methods of sterilizing containers are known from the prior art.

BACKGROUND

WO 2007/145561 A1 describes a method of sterilizing containers. In this case the container is divided into two regions to be sterilized and these two regions are sterilized by electron beam apparatus in the two regions.

An electron gun, which is capable of being introduced into the interior of a container through the opening thereof, is known from WO 2007/095205 A2.

WO 97/07024 describes a method of sterilizing product containers. In this case an electron gun is provided in the form of tubes and the sterilization is carried out by an electron beam. DE 101 34 037 A1 describes an apparatus and a method of plasma sterilization. EP 1 120 121 A2 describes an apparatus for the sterilization of containers by means of ultraviolet light.

A technique for the internal sterilization of a container by means of electrons is known from DE 198 82 252 T1. In this case an electron radiation source is provided which directs the radiation into the interior of the container from the outside. However, in the case of the apparatus described here, which are guided into the interior of a container—for example through the opening—in order subsequently to sterilize the inner wall, various problems arise, particularly with respect to heating.

It may be desirable to make available an apparatus and a method which permit an efficient sterilization even at high levels of performance.

SUMMARY

An apparatus according to the invention for the sterilization of containers has a treatment head which has an exit window through which charge carriers can pass. In addition, the apparatus has a charge-carrier generation source which generates charge carriers, and an acceleration device which is arranged above the exit window and which accelerates the charge carriers in the direction of the exit window. In addition, the apparatus has a cooling device for cooling the exit window. According to the invention the cooling device has a supply opening for a medium, more particularly a gaseous medium, which supply opening is arranged below the exit window and which directs the gaseous medium onto the exit window from below at least in part.

An arrangement of the acceleration device above the exit window is to be understood as being that, in a customary operation in which the apparatus is guided from above through the opening of a container into the interior thereof, the acceleration device is provided above the exit window. If the apparatus is introduced into the container from below in the case of other arrangements, the acceleration device would be arranged below the exit window in a corresponding manner. It is proposed according to the invention, however, that the acceleration device should be arranged on one side of the exit window and the supply opening on an opposite side with respect to the exit window.

The exit window or a plane of the exit window is thus arranged between the supply opening and the acceleration device. In this way, the cooling device or the supply opening is arranged in the same plane in which the charge carriers are also present which have passed through the exit window.

Directing the gaseous medium in part from below is to be understood as being that the gaseous medium has at least one direction of flow which does not extend in the plane of the exit window but strikes the latter at least obliquely from below. In this way, a flow device of the gaseous medium also has a component which is at a right angle to the exit window.

It is preferable for the cross-section of the treatment head to be designed in such a way that the treatment head is capable of being passed through the opening of the container and the acceleration device accelerates the charge carriers in such a way that the charge carriers emerging from the exit window are capable of being directed onto an inner wall of the container. It is preferable for the charge carriers to be electrons.

In this context, reference is made to the European Patent Application No. 07 007 977.7, not yet published, of the Applicants, the contents of the disclosure of which are hereby given entirely with reference to the contents of the disclosure of the present application.

It is preferable for the gaseous medium to be selected from a group of gaseous media which includes air, helium, nitrogen, argon, carbon dioxide, mixtures thereof or the like. The exit window and the acceleration device are preferably arranged inside a housing and this housing is designed in such a way that it is capable of being guided through the opening of the container.

In the case of a further advantageous embodiment the apparatus has an inner housing, inside which the acceleration device is preferably received, and an outer housing, which surrounds this inner housing. It is preferable for a space, which extends as far as the treatment head and through which the gaseous medium is capable of being conveyed for cooling the exit window, to be formed between the outer housing and the inner housing. In this way the cooling medium is preferably conveyed in the space formed in a substantially peripheral manner between the inner housing and the outer housing.

In the case of a further advantageous embodiment the cooling device has at least one supply tube for the gaseous medium, which extends at least in part and preferably substantially completely below the exit window. In this way the gaseous medium is first deflected into a region which is situated below the exit window and is then directed from below onto the exit window. In this way it is possible to cool the entire region of the exit window and, in particular, to prevent central regions from being cooled to a lesser degree than other regions.

In the case of a further advantageous embodiment the supply tube has a portion extending in a straight line. It is preferable for this portion extending in a straight line to extend substantially vertically downwards starting from the treatment head. This prevents the supply tube from interfering during the introduction of the apparatus into the containers.

In the case of a further advantageous embodiment the supply tube has a curved portion. It is preferable for the supply tube to be curved substantially in a U shape in this region, i.e. the gaseous medium is deflected at a pre-determined angle at this curved distance, which is between 100° and 200°, preferably between 130° and 190°, particularly preferably between 140° and 180°, and in a particularly preferred manner between 150° and 180°.

As mentioned above, it is preferable for the supply tube to extend at least in part in a longitudinal direction of the apparatus. In this way it is possible for the apparatus and thus the tube to be guided downwards in a particularly convenient manner.

It is preferable for the tube to be joined to the space formed between the inner housing and the outer housing. This means that the gaseous medium which passes through the space is conveyed substantially completely into one or more supply tubes.

It is preferable for an outer wall of the supply tube to be situated further inside in a radial direction of the apparatus than an outer wall of the outer housing.

It is preferable for the apparatus to have a plurality of supply tubes for the gaseous medium. In this case it is preferable for this plurality of supply tubes to be distributed substantially uniformly in the peripheral direction and thus to act upon the exit window with the gaseous medium from a multiplicity of sides. In the case of a further advantageous embodiment at least one cooling tube is produced from a metal and preferably from a high-grade steel such as for example stainless steel. In this way the cooling tubes can withstand even high temperatures. It is also preferable for the outer housing of the apparatus to be formed from a high-grade steel or stainless steel. In a preferred embodiment the inner tube of the tube is formed from titanium. In a particularly preferred manner the exit window consists of a titanium foil.

In the case of a further advantageous embodiment the apparatus has a ring which terminates the space at the bottom and from which at least one supply tube projects. In this way it is made possible for the medium to be conveyed entirely through the supply tube and thus a particularly efficient cooling of the exit window is achieved.

The present invention further relates to a device for the treatment of containers with a plurality of apparatus of the type described above. It is preferable for the device to have a displacement device which displaces the containers in the longitudinal direction of the containers with respect to the apparatus. In addition, it is preferable for the device illustrated to be arranged between an expansion apparatus for the containers and a device for filling the containers.

The present invention further relates to a method of sterilizing containers, in which in an apparatus of the type described above for the sterilization of containers charge carriers are generated and accelerated in the direction of an exit window which is arranged on a treatment head, and in which the exit window is cooled by a cooling device. It is preferable for a cooling device to direct a gaseous medium onto the exit window at least in part from below by way of a supply opening for the gaseous medium which is situated below the exit window.

It is preferable for the gaseous medium to flow through a supply tube arranged at least in part below the exit window. In the case of a further preferred method the gaseous medium flows at least in part around the inner housing in which the exit window is situated.

It is preferable for the apparatus for sterilization to be introduced into the interior of the container to be sterilized, in order to sterilize the inner wall of the container. In this case it is preferable for the apparatus to be introduced into the container through an opening in the latter. It is also preferable for the apparatus to be moved in the longitudinal direction of the container with respect thereto during the sterilization procedure, in which case both the apparatus and the container can be moved.

Further advantages and embodiments may be seen in the accompanying drawings.

DETAILED DESCRIPTION

Figure 1:
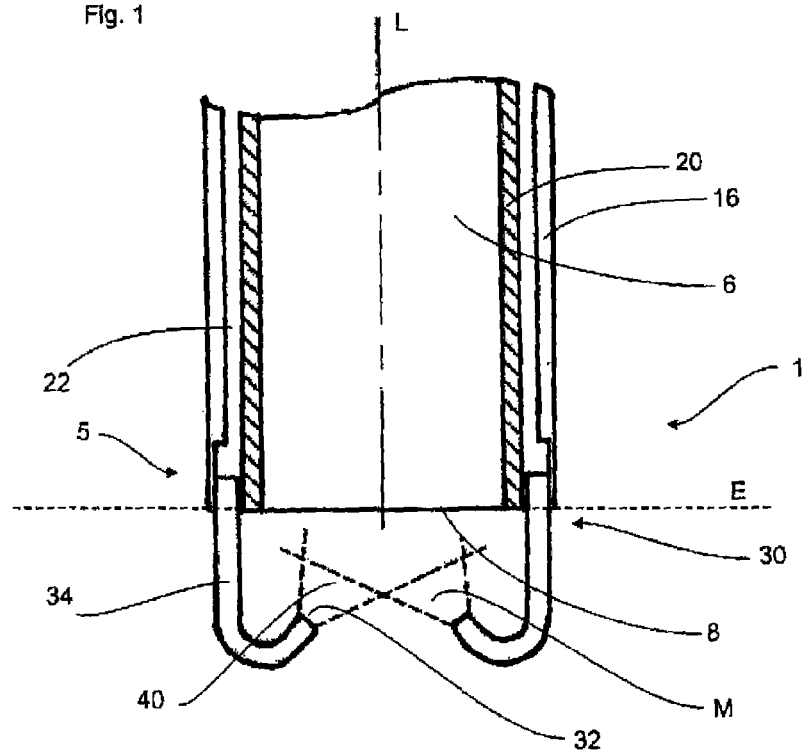
FIG. 1 is a diagrammatic illustration of part of an apparatus according to the invention.

FIG. 1 is a cut-away illustration of an apparatus 1 according to the invention for the sterilization of containers. This apparatus 1 has at the lower end thereof a treatment head which is designated 5 in its entirety and on which is provided an exit window 8 by way of which an electron beam can emerge. In this case, as customary in the prior art, the electrons are first generated for example with the aid of a tungsten cathode. These electrons are then accelerated by way of an acceleration device 6 (not shown in detail). In this case it is possible for electron sources in the form of dots or even surfaces to be used as the electron-generation source. The apparatus 1 for the sterilization of containers has an outer housing 16 and an inner housing 20. In this case, in the embodiment shown in FIG. 1 these two housings are designed in each case with an essentially circular cross-section. In this way the apparatus is constructed with double walls, in which case a continuous gap 22, along which in particular air or another gaseous medium or optionally even a liquid medium can be conveyed, is formed between the outer housing 16 and the inner housing 20. Instead of a continuous gap, however, it would also be possible for a plurality of channels to be provided which extend in particular in the longitudinal direction L of the apparatus.

A cooling device designated 30 in its entirety adjoins these channels or the air gap 22 respectively. In this case this cooling device 30 has a plurality of cooling tubes 34 which first extend in the longitudinal direction L and then over a curved portion are formed in such a way that the gaseous medium M can be directed from below through an opening 32 onto the exit window 8 in order to cool the latter. As a result of this design it is made possible for a central region of the exit window 8 in particular also to be cooled in a satisfactory manner.

In this case it is possible for the gas jet M to be directed onto the exit window 8 during the operation of the apparatus, but it is also possible for the gas flow to be directed onto the exit window in the period of time in which the apparatus is not active or the radiation source is not active. In this way it is possible to prevent the emerging electron beam from being influenced by the air flow. It is pointed out in this case that the gas flow is used for cooling the exit window and, in particular, not for guiding the electron beam.

In principle, the beam flow is the decisive factor in the case of an optimally selected acceleration voltage, in order to generate the correspondingly required dose in the container in the shortest possible time. This beam flow, however, results in losses in the exit window 8 which, depending upon the design of this exit window 8, also limit the maximum radiation power of the electron radiation unit or the apparatus 1 sooner or later. With the air, gas or liquid cooling described, however, the necessary cooling of the exit window can be provided. In other words, in order to achieve the maximum possible beam flow, i.e. the maximum possible throughput, the number of the radiation units should be minimized or the clock time should be increased. In addition, it would be possible to improve the scatter geometry on the atmosphere, i.e. outside the exit window 8.

The electrons are accelerated at energy in a range of from 100 keV to 200 keV, preferably between 120 keV and 180 keV and preferably 130 keV and 170 keV.

In the interior of the apparatus or in the interior of the inner housing or inner tube 20 it is possible for deflecting devices to be provided which deflect the electron beam in a radial direction inside the inner housing 20. In this case for example the inner housing 20 can have an end portion enlarged in a tapered manner in the region of the treatment head. Because of this end portion it is possible to deflect the electron beams at a relatively high angle.

In addition, spacer members can be provided between the inner housing 20 and the outer housing 16, and they prevent contact between the inner housing and the outer housing and result in thermal insulation. It is also preferable for the spacer members to be insulated electrically.

In the case of the embodiment shown in FIG. 1 the exit window 8 is situated in a plane which is indicated by the broken line E and is situated at a right angle to the plane of the figure. It would also be possible, however, for the exit window to be arched and, in particular, to be arched towards the inside.

Figure 2:
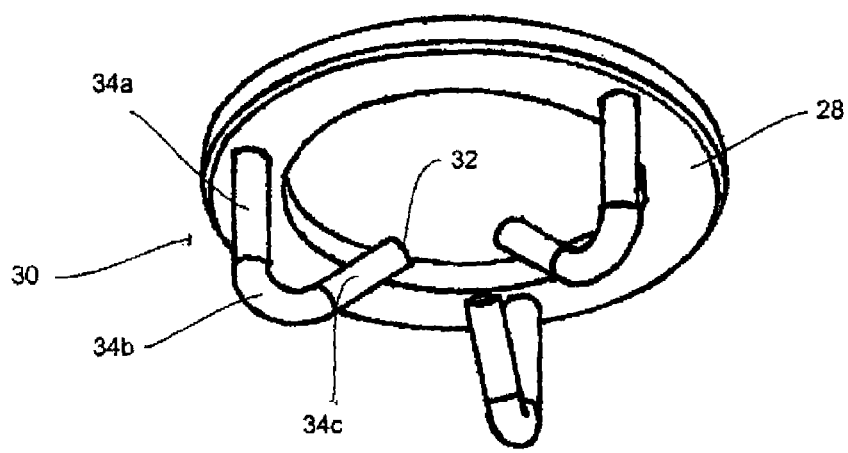
FIG. 2 is a detailed illustration of a cooling device for the apparatus as shown in FIG. 1.

FIG. 2 is a detailed illustration of part of a cooling device 30 according to the invention. In this case the reference number 28 designates a cover which can be arranged at the lower end of the apparatus 1 shown in FIG. 1. Three cooling tubes 34 extend in this case out of this cover 28 which substantially covers the gap 22. These cooling tubes 34 have a first portion 34a which extends in the longitudinal direction L of the apparatus, a second curved portion 34b and a third portion 34c, again extending in a straight line, which has the effect that the air or gas flow is directed obliquely onto the exit window 8 from below by way of an exit opening 32. In this case the curved portion 34 causes a curvature of between 100° and 180°, preferably between 100° and 170°, and in a particularly preferred manner between 130° and 170°. In the case of the embodiment shown in FIG. 2 three cooling tubes 34 of this type are shown, which are uniformly distributed over the external periphery of the ring 28 or cover. It would also be possible, however, for a different number of cooling tubes to be used and, in addition, the curvature of individual cooling tubes 34 in the region 34b could differ from one another.

All the features disclosed in the application documents are claimed as being essential to the invention, insofar as they are novel either individually or in combination as compared with the prior art.

What is claimed is:

1. An apparatus for the sterilization of containers, comprising:
   a treatment head having an exit window through which charge carriers are permitted to pass;
   a charge-carrier generation source which generates charge carriers;
   an acceleration device arranged above the exit window, the acceleration device accelerating the charge carriers in the direction of the exit window;
   an inner housing, the acceleration device being received inside the inner housing;
   an outer housing surrounding the inner housing, a space formed between the outer housing and the inner housing, the space extending as far as the treatment head; and
   a ring which terminates the space, and from which at least one supply tube projects downward, wherein each supply tube directs a cooling medium upward toward a center of the ring for cooling the exit window, the cooling medium being carried to the supply tube through the space.

2. An apparatus according to claim 1, further comprising a cooling device for cooling the exit window, wherein the cooling device includes at least one supply tube for the medium, the at least one supply tube extending at least in part below the exit window.

3. An apparatus according to claim 2, wherein the supply tube includes a portion extending in a straight line.

4. An apparatus according to claim 2, wherein the supply tube includes a curved portion.

5. An apparatus according to claim 2, wherein the supply tube extends at least in part in a longitudinal direction of the apparatus.

6. An apparatus according to claim 2, wherein the supply tube is joined to the space.

7. An apparatus according to claim 2, wherein the cooling device includes a plurality of supply tubes.

8. An apparatus according to claim 2, wherein at least one cooling tube is produced from a metal.

9. An apparatus according to claim 8, wherein the metal is stainless steel.

10. An apparatus according to claim 2, further comprising a ring which terminates the space and from which at least one supply tube projects.

11. An apparatus according to claim 2, wherein the exit window or a plane of the exit window is arranged between the supply opening and the acceleration device.

12. An apparatus according to claim 2, wherein the supply tube is curved at a predetermined angle between 100° and 170°.

13. An apparatus according to claim 2, wherein an outer wall of the supply tube is situated further inside in a radial direction of the apparatus than an outer wall of the outer housing.

14. A device for the treatment of containers, the device comprising a plurality of apparatuses according to claim 1.

15. An apparatus according to claim 1, wherein the exit window comprises a titanium foil.

\* \* \* \* \*